(12) United States Patent
Kuroda

(10) Patent No.: US 8,843,191 B2
(45) Date of Patent: Sep. 23, 2014

(54) METHOD FOR MEASURING AND IMAGING TEMPERATURE DISTRIBUTION IN TISSUE

(75) Inventor: Kagayaki Kuroda, Yokohama (JP)

(73) Assignee: Koninklijke Philips N.V., Eindhoven (NL)

( * ) Notice: Subject to any disclaimer, the term of this patent is extended or adjusted under 35 U.S.C. 154(b) by 156 days.

(21) Appl. No.: 13/498,625

(22) PCT Filed: Sep. 29, 2010

(86) PCT No.: PCT/JP2010/066909
§ 371 (c)(1),
(2), (4) Date: Jul. 9, 2012

(87) PCT Pub. No.: WO2011/040439
PCT Pub. Date: Apr. 7, 2011

(65) Prior Publication Data
US 2012/0271152 A1    Oct. 25, 2012

(30) Foreign Application Priority Data
Sep. 29, 2009 (JP) ................ 2009-224432

(51) Int. Cl.
*A61B 5/055* (2006.01)
*G01V 3/00* (2006.01)
*A61B 5/00* (2006.01)
*A61B 5/01* (2006.01)

(52) U.S. Cl.
CPC . *A61B 5/01* (2013.01); *A61B 5/055* (2013.01); *A61B 5/4869* (2013.01)
USPC .......................................... 600/412; 324/309

(58) Field of Classification Search
USPC .......... 600/407, 409, 410, 412, 549; 324/307, 324/308, 309, 315
See application file for complete search history.

(56) References Cited

U.S. PATENT DOCUMENTS 6,618,608 B1 * 9/2003 Watkins et al. ............... 600/412
7,505,805 B2    3/2009 Kuroda

OTHER PUBLICATIONS

K. Kuroda et al, Temperature Dependence of Relaxation Times in Individual Fatty Acid Components and Its Consideration for Mr Thermometry of Adipose Tissues, Proc. Intl. Soc. Mag. Reson. Med. 17, 2009.04, #2533.*

Crawley, Adrian et al "A Comparison of One-Shot and Recovery Methods in TI Imaging", Magnetic Resonance in Medicine, vol. 7, 1988, pp. 23-34.

Johnson, K. M. et al "Absolute Temperature Imaging with Non-Linear Fat/Water Signal Fitting", Proc. Intl. Society Magnetic Resonance in Medicine, vol. 16, 2008, pp. 1236.

(Continued)

*Primary Examiner* — Michael Rozanski

(57) ABSTRACT

Disclosed are a method for measuring temperature distribution, which measures temperature distribution not only in fat tissue but also in mixed tissue containing high-water content tissue and fat tissue, and a method for imaging temperature distribution. In the disclosed method, a water signal, which is dependent on the water components of the tissue to be measured, and a fat signal, which is dependent on the fat components of the tissue to be measured, are acquired by means of nuclear magnetic resonance spectroscopy. Fatty acid signals are acquired by separating out the fat signal into various fatty acid components. The temperature of high-water content tissue is measured on the basis of the correlation between the water signal and the water temperature, and the temperature of fat tissue is measured on the basis of the correlation between each of the various fatty acid signals and the fat temperature.

6 Claims, 7 Drawing Sheets

(56) References Cited

OTHER PUBLICATIONS

Hynynen, Kullervo et al "Temperature Monitoring in Fat with MRI", Magnetic Resonance in Medicine, vol. 43, No. 6, 2000, pp. 901-904.
Chen, Jing et al "Investigation of Proton Density for Measuring Tissue Temperature", Journal of Magnetic Resonance Imaging, vol. 23, No. 3, 2006, pp. 430-434.
Bluml, Stefan et al "Spin-Lattice Relaxation Time Measurement by Means of a TurboFLASH Technique", Magnetic Resonance in Medicine, vol. 30, 1993, pp. 289-295.

* cited by examiner (a)

(b)

(c)

US 8,843,191 B2

METHOD FOR MEASURING AND IMAGING TEMPERATURE DISTRIBUTION IN TISSUE

TECHNICAL FIELD

The present invention relates to a method for measuring temperature distribution, which measures the temperature distribution in tissue to be measured, said tissue to be measured being either fat tissue or mixed tissue containing high-water content tissue and fat tissue, by means of proton ($^1$H) Nuclear Magnetic Resonance (hereinafter, simply referred to as NMR) and to a method for imaging temperature distribution, which creates temperature distribution images on the basis of the measured temperature distribution.

BACKGROUND ART

Thermotherapy such as hyperthermia, thermal ablation, and thermal cancer necrosis is one of cancer treatment modalities. Such thermotherapy treats cancer through the method of destroying tissue in area to be treated by heating the area to be treated above a certain temperature.

For example, a specific method of thermotherapy includes a technique called "dielectric heating", which heats the area to be treated by applying a high-frequency current thereto, and focused ultrasound technique, which heats the area to be treated by focusing ultrasound thereon.

In performing such a thermotherapy, there may be a rise in temperature even in the non-target area around the target area to be treated at the same time, which may influence the therapeutic effect, thus it is required to measure the temperatures of a wide range of tissues including the target area to be treated as well as the non-target area rapidly and accurately.

Conventionally a temperature measurement in the thermotherapy has been performed by positioning a probe such as a thermocouple at and around the area to be treated. However, for such an invasive temperature measurement technique, there might be a concern about impact on the non-target area, thus there has been a need for a noninvasive temperature measurement technique.

Accordingly, as disclosed in a patent document 1, a method for measuring and imaging the tissue temperature distribution by means of water-proton nuclear magnetic resonance signals (water signals) has been proposed.

Such a method for imaging the temperature distribution focuses on a water proton chemical shift in phase mapping or nuclear magnetic resonance spectroscopic imaging by means of NMR equipment to image variation in temperature thereof. This method is now practically used only in temperature distribution measurement of for example less fluctuating high-water content tissue.

In contrast, for example in focused ultrasound therapy of breast cancer, the target tissues to be measured is the mammary gland, which is high-water content tissue, and the breast, which is a mixture of high-water content tissue and fat tissue.

Imaging of the temperature distribution in fat tissue with low water content by acquiring a water signal, however, has not been practically used in view of incomplete signal separation, partial volume effect, and signal-to-noise ratio (hereinafter, simply referred to as S/N ratio).

Therefore, as described in non-patent documents 1 to 3, a technique for measuring the temperature of fat tissue by means of a NMR signal has been proposed.

This measuring method enables the temperature measurement using the longitudinal relaxation time ($T_1$) and intensity of an integrated signal over fat tissue without observing the frequency spectrum (chemical shift) of fat tissue.

DESCRIPTION OF THE RELATED ART

Patent Document 1 JP-A-2005-46588
Non-Patent Document 1 Hynynen K, McDannaold N, Mulkern R V, Jolesz F A, "Temperature monitoring in fat with MRI", Magn Reson Med 2000; 43 (6): 901-904
Non-Patent Document 2 Chen J, Daniel B L Pauly K B, "Investigation of proton density for measuring tissue temperature", J Mann Reson Imaging 2006; 23 (3): 430-434
Non-Patent Document 3 K. M. Johnson, V. Chebrolu, and S. B. Reeder, "Absolute Temperature Imaging with Non-Linear Fat/Water Signal Fitting" (2008)
Non-Patent Document 4 Kagayaki Kuroda, Makoto Obara, Cauteren M V, "Temperature Dependence of Relaxation times in Individual Fatty Acid Components and Its Application to Temperature Distribution Imaging", Japanese Journal of Magnetic Resonance in Medicine (2008)
Non-Patent Document 5 Stefan Bluml, Lothar R. Schad, Boris Stepanow, Walter J. Lorenz, "Spin-Lattice Relaxation Time Measurement by Means of a TurboFLASH Technique", MRM 30:289-295 (1993)
Non-Patent Document 6 ADRIAN P. CRAWLEY and R. MARK HENKELMAN, "A Comparison of One-Shot and Recovery Methods in T1 Imaging", MAGNETIC RESONANCE IN MEDICINE 7, 23-34 (1988)

SUMMARY OF INVENTION

Generally, observing frequency spectrum of the proton ($^1$H) NMR signal of fat tissue, it can be separated out into about ten frequency components, which are dependent on binding form of carbon and hydrogen forming the chemical structures of various kinds of fatty acids, for example the difference in structure of hydrocarbon groups, such as a $CH_3$ group, a $CH_2$ group, and a CH group. These hydrocarbon group components are, herein, referred to as fatty acid components.

However, when the fat temperature was measured without observation of the frequency spectrum of fat tissue, no obvious temperature dependency was shown, resulting in failure to measure the temperature quantitatively.

A non-patent document 4, as shown in FIG. 3, describes that a correlation was obtained between the longitudinal relaxation time ($T_1$) of each fatty acid component, in particular, the $CH_2$ group component and $CH_3$ group component signals and the temperature by observing the frequency spectrum of fat tissue and separating out the signal into each fatty acid component.

It is also described that a plurality of temperature-dependent NMR parameters for each fatty acid component include resonance center frequency, intensity, full width at half maximum (FWHM), longitudinal relaxation time ($T_1$), transverse relaxation time ($T_2$), diffusion constant (D), or the like.

However, the non-patent document 4 describes only the correlation between the longitudinal relaxation time ($T_1$) of each fatty acid component and the temperature but no feasible method for measuring the temperature distribution of the tissue containing at least one of high-water content tissue and fat tissue.

A primary object of the present invention is to provide a method for measuring the temperature distribution and a method for imaging the temperature distribution to measure the temperature distribution of fat tissue by measuring the temperature-dependent parameters for each fatty acid component as well as to apply to the mixed tissue of high-water content tissue and fat tissue and measure the temperature distribution thereof.

Another object of the present invention is to provide a method for measuring the temperature distribution and a method for imaging the temperature distribution with only a small error in temperature measurement even for the mixed tissue of high-water content tissue and fat tissue, and which is also able to be practically used in temperature measurement in for example focused ultrasound therapy of breast cancer.

Solution to Problem

The method for measuring temperature distribution of the present invention, which has been invented to achieve above-mentioned objects, measures the temperature distribution in tissue to be measured, said tissue to be measured being either fat tissue or mixed tissue containing high-water content tissue and fat tissue; acquires a water signal, which is dependent on water components of the tissue to be measured, and a fat signal, which is dependent on fat components of the tissue to be measured, by mean of NMR, and separates out the fat signal into various fatty acid components having a different hydrocarbon structure to acquire various fatty acid signals; and measures the temperature of the high-water content tissue on the basis of a correlation between the water signal and water temperature, and measures the temperature of the fat tissue on the basis of the correlation between at least one of the various fatty acid signals and fat temperature.

Further the method for measuring the temperature distribution of the present invention divides the tissue to be measured into measurement units of given size and acquires the water signal and the fat signal for each measurement unit to measure the temperature of the fat tissue for each measurement unit.

Further the method for measuring the temperature distribution of the present invention calculates a weighted average of the water temperature and the fat temperature obtained for each measurement unit on the basis of the contents of the water components and the fat components of the tissue to be measured for each measurement unit so as to be used as temperature of the tissue to be measured for each measurement unit.

Further the method for measuring the temperature distribution of the present invention measures the temperature of the fat tissue by means of a $CH_2$ group proton dependent signal (herein, also referred to as a $CH_2$ group dependent signal; this is applicable to other fatty acid signals) and/or a $CH_3$ group dependent signal among the various fatty acid signals.

Further the method for measuring the temperature distribution of the present invention measures a longitudinal relaxation time for each of the various fatty acid components by any one of a multiple flip angle method, an inversion recovery method, and a saturation recovery method so as to be used as a correlation parameter between each of the various fatty acid signals and the fat temperature.

Further the method for imaging the temperature distribution of the present invention creates temperature distribution images by converting the temperature highs and lows in the temperature distribution of the tissue to be measured which is measured by the above-mentioned method of measuring the temperature distribution into signal intensity so as to be mapped.

Advantageous Effect of Invention

According to the present invention, the temperature may be accurately measured with a small measurement error by separating out the NMR signal into various fatty acid components and using a temperature dependent parameter for at least one of these fatty acid components in measuring the temperature distribution not only in fat tissue but also in the mixed tissue containing the high-water content tissue and fat tissue.

DESCRIPTION OF EMBODIMENT

Referring to the accompanying drawings, an embodiment of the present invention is in detail described below.

Figure 1:
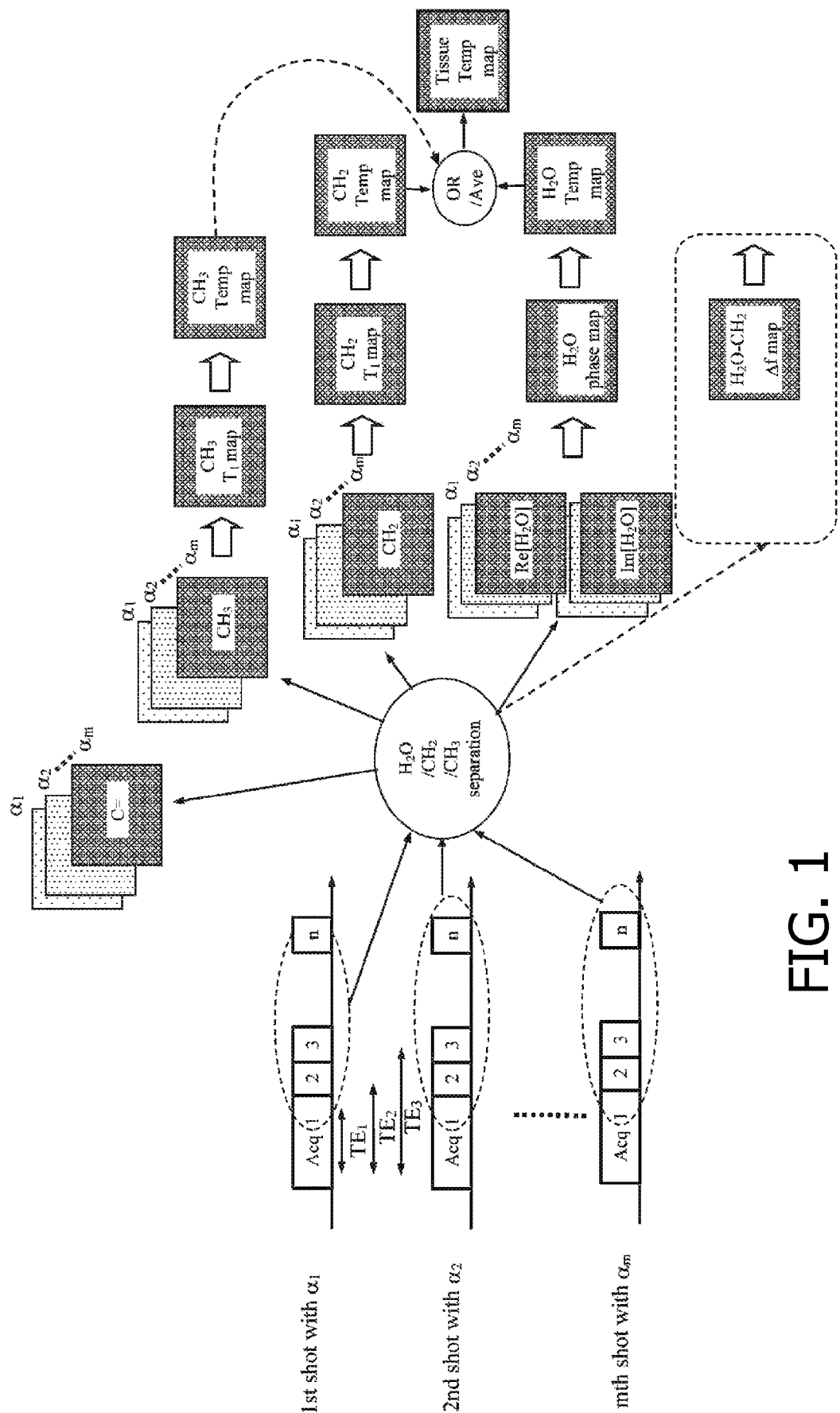
FIG. 1 is a schematic drawing illustrating a flow of the step of creating the temperature distribution images of the tissue to be measured by the method for measuring the temperature distribution of the present invention.

FIG. 1 is a schematic drawing illustrating a flow of the step of creating the temperature distribution images of the tissue to be measured by the method for measuring the temperature distribution of the present invention.

In this embodiment, the temperature distribution in a given cross section is measured with the mixed tissue containing the high-water content tissue and fat tissue as a tissue to be measured to create the temperature distribution images.

In order to measure the temperature distribution in the cross section of the tissue to be measured, firstly the cross section is divided into measurement units of given size. It is preferred to set the measurement unit appropriate for the device configuration, because temperature measurement is performed for each measurement unit, thereby, a small measurement unit enables detailed temperature measurement to be performed, while an S/N ratio is reduced leading to deteriorated measurement accuracy. In this way the temperature measured for each measurement unit is subsequently imaged and displayed in the form of temperature distribution over the whole tissue to be measured.

Then, the signal due to variation in longitudinal magnetization for each measurement unit is read out by the multiple flip angle method for the tissue to be measured. The measurement with an echo time (TE) varied ($TE_1$, $TE_2$, ... $TE_m$) respectively for a plurality of flip angles enables all the signals necessary for creating temperature distribution images to be read out in a very short period of time.

The number of variations in flip angle and in echo time during measurement may be not particularly limited, but assuming that the signals are acquired at, for example, two flip angles during five periods of echo time, the signals necessary for creating the temperature distribution images would be acquired rapidly and accurately.

Figure 2:
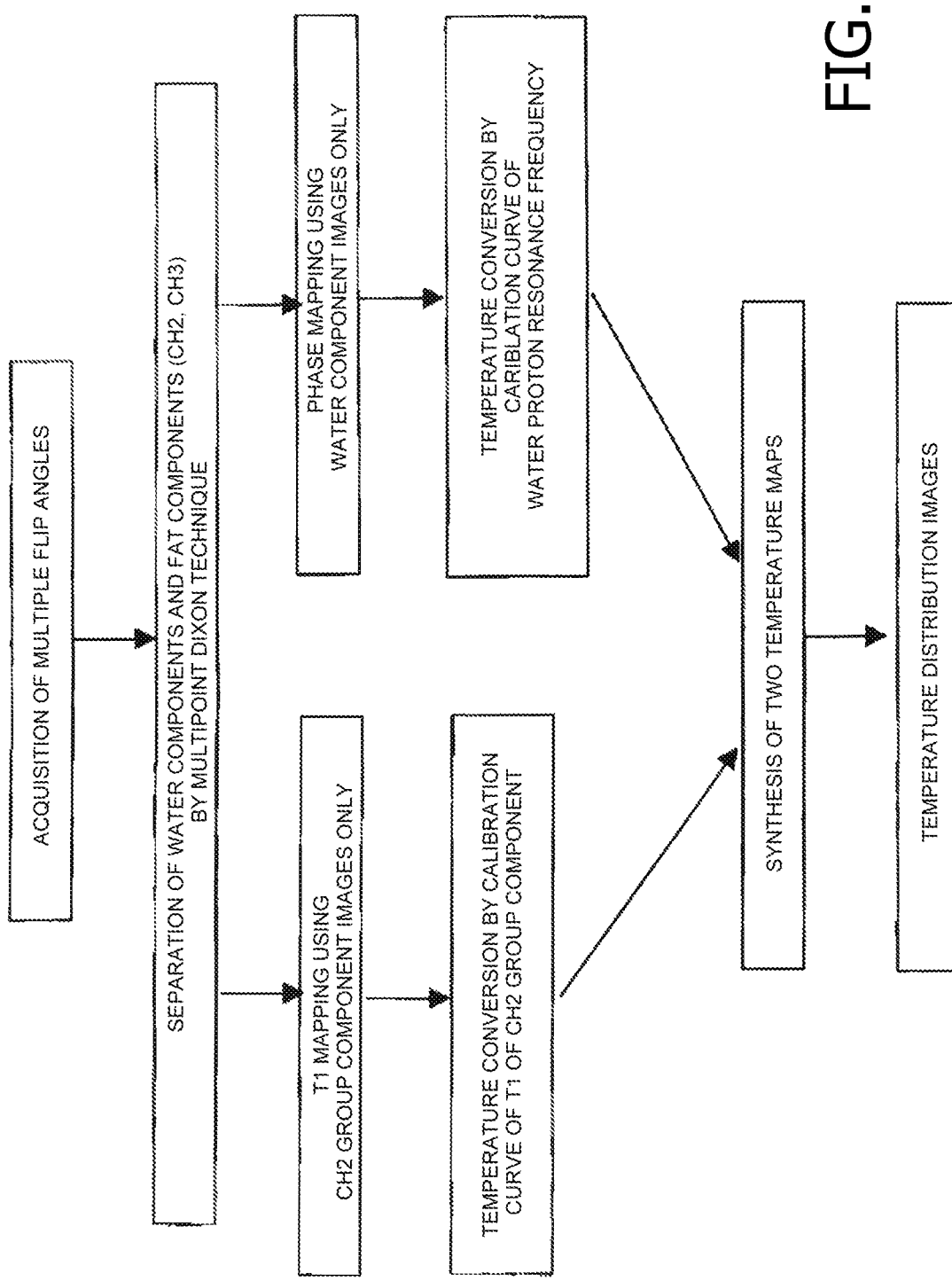
FIG. 2 is a flowchart of an algorithm for estimating the temperature on the basis of the longitudinal relaxation time ($T_1$) of a $CH_2$ group and the NMR frequency of water using multiple flip angle method.

FIG. 2 is a flowchart of an algorithm for estimating the temperature on the basis of the longitudinal relaxation time ($T_1$) of the $CH_2$ group and the NMR frequency of water by the multiple flip angle method.

As shown in the flowchart of FIG. 2, the signal acquired by the multiple flip angle method is separated out into the water signal and the fat signal by Multipoint Dixon technique, and the fat signal is further separated out into a $CH_2$ group dependent signal, which is dependent on a $CH_2$ group, and a $CH_3$ group dependent signal, which is dependent on a $CH_3$ group.

This process is applied to the images obtained at all the flip angles (for example, $\alpha_1, \alpha_2, \ldots, \alpha_{10}$) to measure the longitudinal relaxation time ($T_1$) of the $CH_2$ or $CH_3$ group.

Figure 3:
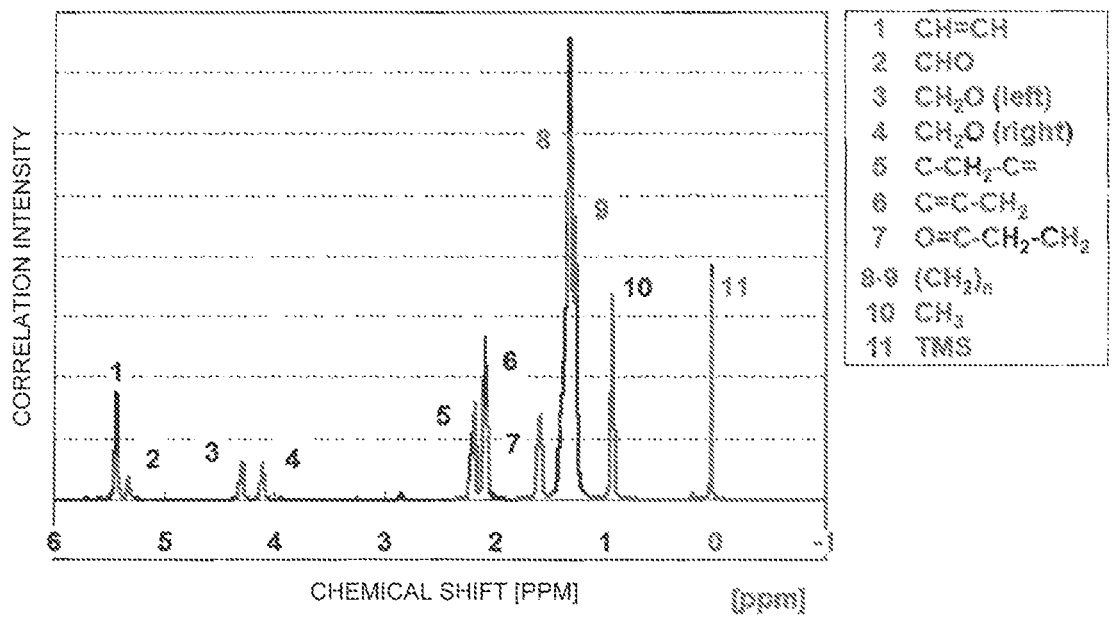
FIG. 3 is a view showing the correlation between the longitudinal relaxation times ($T_1$) of the signals of and the temperatures of respective fatty acid components, in particular, $CH_2$ group and $CH_3$ group components, which were separated from olive oil by means of nuclear magnetic resonance spectroscopy (($_1$H NMR) as described in the non-patent document 4.
Figure 3:
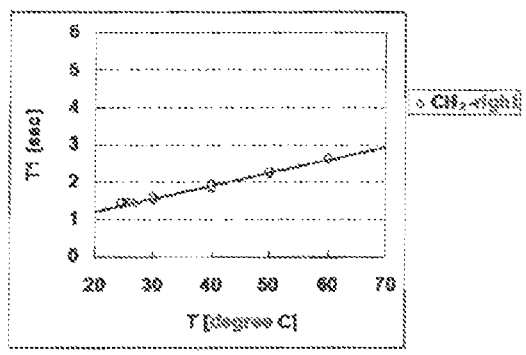
Figure 3:
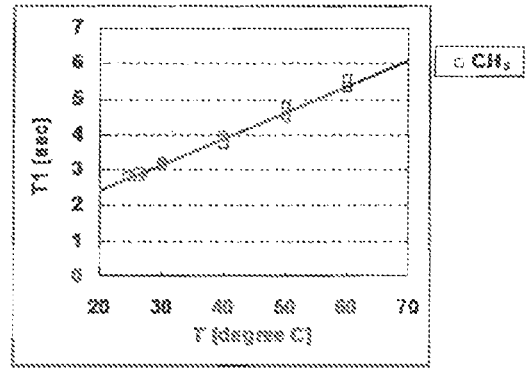
Figure 4:
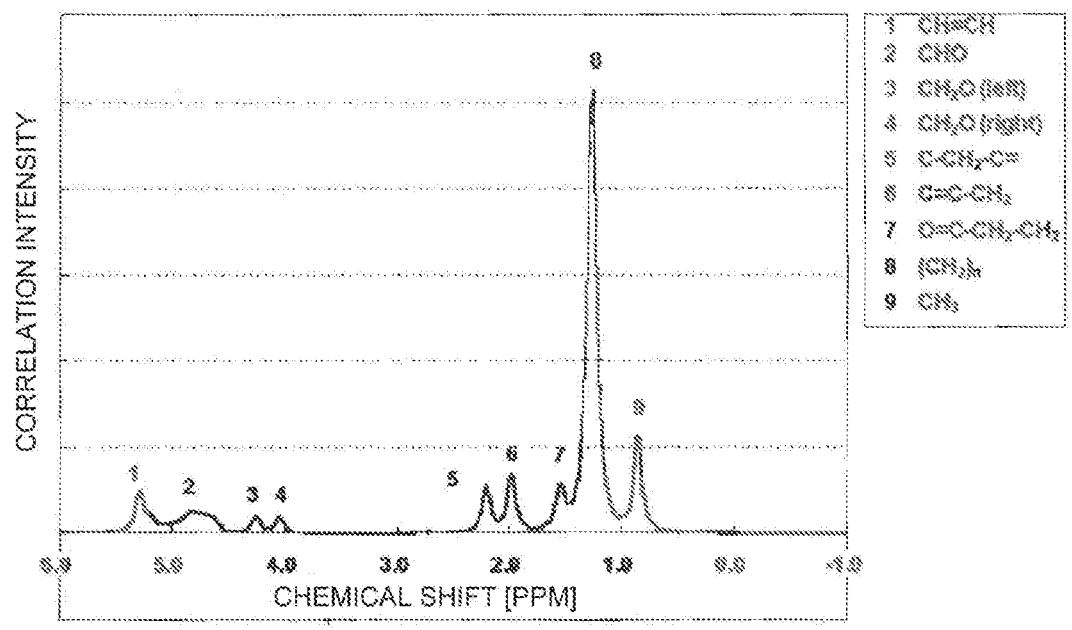
FIG. 4, as in FIG. 3, is a view showing the correlation between the longitudinal relaxation times ($T_1$) of the signals of and the temperatures of respective fatty acid components, in particular, $CH_2$ group and $CH_3$ group components, which were separated from bovine fat by means of $_1$H NMR.
Figure 4:
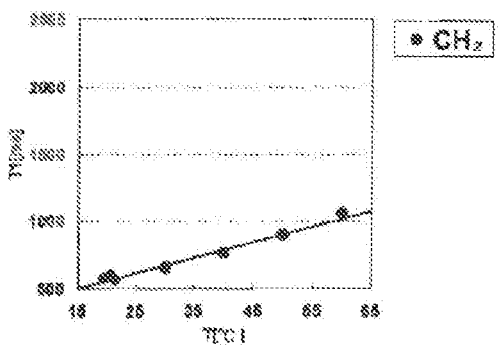
Figure 4:
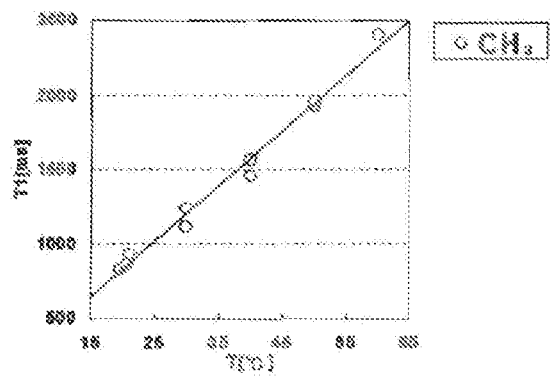

Then the fat temperature for each measurement unit is determined on the basis of the temperature dependency of the longitudinal time ($T_1$) of the $CH_2$ or $CH_3$ group obtained in this way, namely on the basis of the correlation between the longitudinal relaxation times ($T_1$) and the temperatures as shown in FIGS. 3 and 4.

FIG. 3 (a) is a view showing the relationship between the longitudinal relaxation time ($T_1$) and temperature of each fatty acid component separated from olive oil by means of $_1M$ NMR, as described in the non-patent document 4, FIG. 3 (b) is a view showing the correlation between the longitudinal relaxation time ($T_1$) of $CH_2$ group component signal and temperature, and FIG. 3 (c) is a view showing the relationship between the longitudinal relaxation time ($T_1$) of $CH_3$ group component signal and temperature.

FIG. 3 (b) shows that the correlation observed between the longitudinal relaxation time ($T_1$) of the $CH_2$ group component signal and the temperature is 34 ms/° C. Also, FIG. 3 (c) shows that the correlation observed between the longitudinal relaxation time ($T_1$) of the $CH_3$ group component signal and the temperature is 74 ms/° C.

As in FIG. 3, FIG. 4 is a view showing the correlation between the longitudinal relaxation time ($T_1$) of the signal and temperature of each fatty acid component, in particular, $CH_2$ group and $CH_3$ group components, which were separated from bovine fat by means of $_1H$ NMR.

As shown in FIG. 4 (a), the correlation between the longitudinal relaxation time ($T_1$) of the signal of and the temperature of each fatty acid component, in particular, the $CH_2$ group component as shown in FIG. 4 (b) and the $CH_3$ group component as shown in FIG. 4 (c), may be observed by separating each fatty acid component from bovine fat by means of nuclear magnetic resonance spectroscopy and detecting the signal thereof.

FIG. 4 (b) shows that the correlation observed between the longitudinal relaxation time ($T_1$) of the $CH_2$ group component signal and the temperature is 11.5 ms/° C. Also, FIG. 4 (c) shows that the correlation observed between the longitudinal relaxation time ($T_1$) of the $CH_3$ group component signal and the temperature is 37.1 ms/° C.

Figure 5:
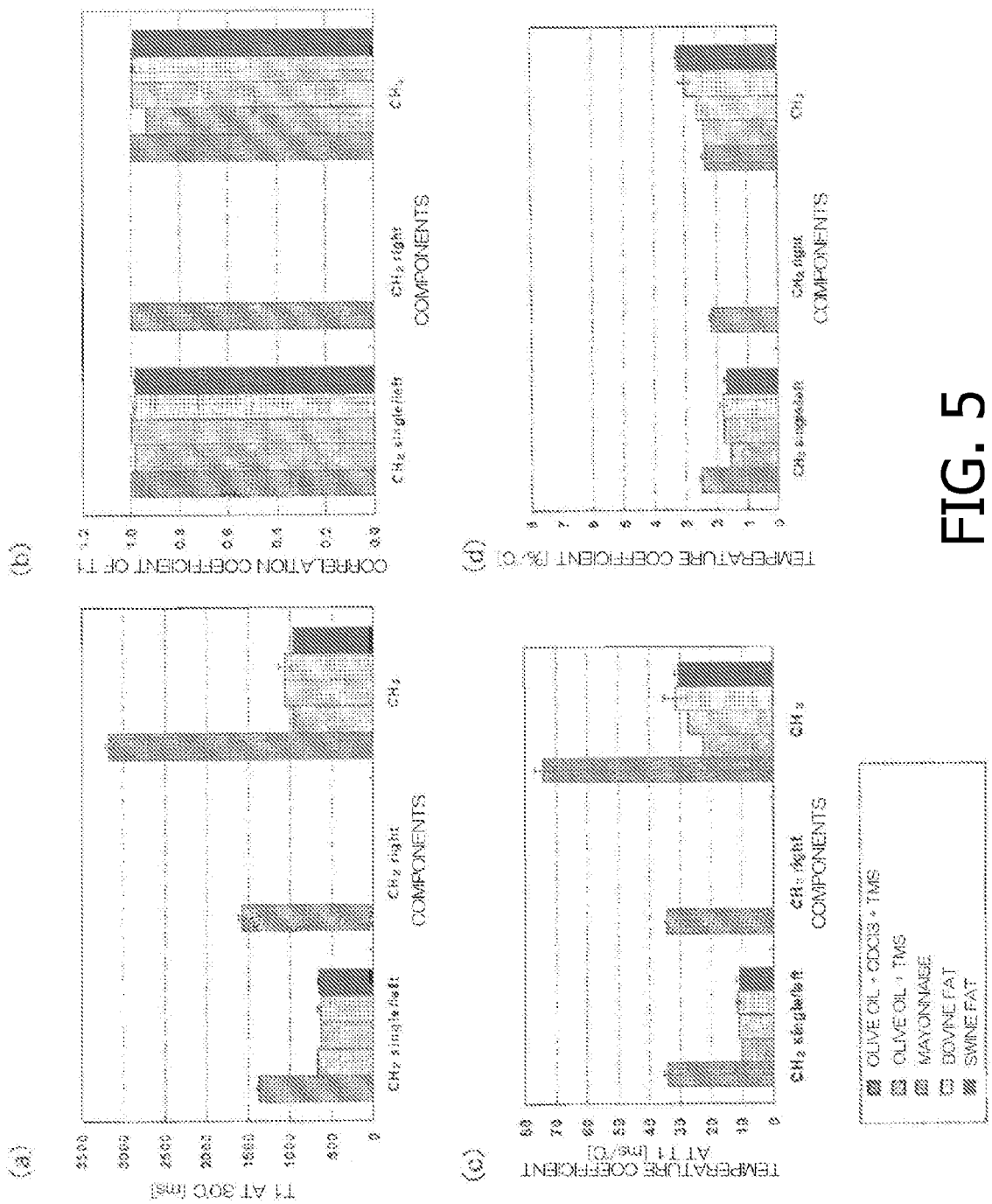
FIGS. 5 (a), 5 (b), 5 (c), and 5 (d) are graphs showing: (a) the absolute values at 30° C.; (b) the correlation coefficients with temperature; (c) the temperature coefficients [ms/° C.]; and (d) the relative temperature coefficients [%/° C.] with respect to the absolute values at 30° C., for $T_1$ of the $CH_2$ group and $CH_3$ group component signals, respectively when each fatty acid component is separated and measured by means of $_1$H NMR with respect to olive oil dissolved in a deuterated chloroform solution (tetramethylsilane (TMS) added), olive oil, mayonnaise, bovine fat, and swine fat.

As in FIGS. 3 and 4, FIGS. 5 (a), 5(b), 5(c), and 5(d) respectively show: (a) the absolute value at 30° C.; (b) the correlation coefficient with the temperature; (c) the temperature coefficient [ms/° C.]; and (d) the relative temperature coefficient [%/° C.] with respect to the absolute value at 30° C., for $T_1$ the $CH_2$ group and $CH_3$ group component signals, respectively when each fatty acid component is separated and measured by means of $_1H$ NMR with respect to olive oil dissolved in a deuterated chloroform solution (tetramethylsilane (TMS) added), olive oil, mayonnaise, bovine fat, and swine fat.

Thus, the correlation coefficient between the longitudinal relaxation time ($T_1$) and the temperature even for different kinds of fats indicates almost 1 (one), demonstrating that a preferable correlation is observed between the longitudinal relaxation time and the temperature.

It should be noted that the $CH_2$ group component signal might appear separately as No. 8 and No. 9 signals in FIG. 3, and the signal labeled with "$CH_2$ right" as shown in FIG. 5 is a signal appearing on the right side of the $CH_2$ group component signals in FIG. 3 (a). Therefore, as shown in FIG. 4 (a), when the $CH_2$ group component signal is not separated, the signal is labeled with "$CH_2$ single".

The fat temperature distribution image may be created by converting the fat temperature for each measurement unit for example into a high signal for the high-temperature measurement unit and a low signal for the low-temperature measurement unit and mapping them. In this case, the high signal portion (i.e. high temperature portion) is white and the low signal portion (i.e. low temperature portion) is black in the fat temperature distribution image.

On the other hand, for water signal, the phase distribution of water proton complex NMR signals (the real part image and the imaginary part image of the complex NMR signals) are obtained and the water temperature for each measurement unit is determined on the basis of variation in phase of the complex NMR signal ([0037] to [0044] of the patent document 1).

Then the water temperature distribution image may be created by converting the water temperature for each measurement unit for example into the high signal for the high temperature measurement unit and the low signal for the low temperature measurement unit and mapping them. In this case, the high signal portion (i.e. high temperature portion) is white and the low signal portion (i.e. low temperature portion) is black in the water temperature distribution image.

The temperature distribution image of the tissue to be measured may be created by synthesizing the fat temperature distribution image and the water temperature distribution image obtained in the above-mentioned manner.

To synthesize the fat temperature distribution image and the water temperature distribution image, the weighted average depending on the content of water components and the content of fat components is taken for each measurement unit. More specifically, if only one of the fat temperature and the water temperature is obtained for each measurement unit, the obtained temperature is assumed to be the temperature of the tissue to be measured for the measurement unit, while if both of the fat temperature and the water temperature are obtained, the temperature of the tissue to be measured is calculated on the basis of the rate of fat content and the rate of water content in the measurement unit as shown in Expression 1.

$$Tt = Tf \times Rf + Tw \times Rw \quad \text{[Expression 1]}$$

Where,
the abbreviations have the following meanings:
(Tt: temperature of the tissue to be measured in the measurement unit (° C.), Tf: fat temperature (° C.), Rf: rate of fat content (mass percentage or volume percentage), Tw: water temperature (° C.), and Rw: rate of water content (mass percentage or volume percentage).
In this way the temperature distribution of the tissue to be measured is measured by synthesizing the fat temperature and the water temperature for each measurement unit, thus the temperature distribution may be measured accurately even for the mixed tissue of high-water content tissue and fat tissue.

The embodiment of the present invention uses the mixed tissue containing high-water content tissue and fat tissue as the tissue to be measured; however, when the tissue to be measured only consists of fat tissue, the step of measuring the temperature of the high-water content tissue on the basis of the correlation between the water signal and the water temperature may be omitted.

It should be understood that the embodiment of the present invention uses but not be limited to the multiple flip angle method to obtain the longitudinal relaxation time ($T_1$), the temperature distribution image may be created by for example using the combination of the Look-Locker method and the inversion recovery method, and the saturation recovery method, to obtain the longitudinal relaxation time and separate the water signal, the $CH_2$ dependent signal and the $CH_3$ dependent signal.

Although the preferred embodiment of the present invention has been described, the present invention is not limited thereto, for example only the $CH_2$ group dependent signal and the $CH_3$ group dependent signal are used as various fatty acid signals in the present specification, but not limited thereto, signals on the basis of other fatty acid components for example the hydrocarbon structures such as CH=CH, C—$CH_2$—C=, C=C—$CH_2$ may be used.

Also, the longitudinal relaxation time of each fatty acid component and the water signal may be measured simultaneously, and the time for sampling longitudinal magnetization intensity may be optimized during measurement of the longitudinal relaxation time of each fatty acid component.

Further the variation in each fatty acid signal may be divided at regular intervals with respect to the direction of the variation to sample at the time points corresponding to the division points, and the range of variation in longitudinal magnetization intensity may be optimized with the longitudinal magnetization intensity varied.

Besides, various modifications may be made without departing from the scope and spirit of this invention, for example, the phase distribution from a plurality of echo signals of the water signal may be measured simultaneously with the measurement of the longitudinal relaxation time of each fatty acid component and the water temperature may be calculated by estimating the variation in temperature of water components for obtaining the variation in water proton resonance frequency from the difference between the phase distribution before the variation in temperature of the tissue to be measured and the phase distribution after the variation in temperature of the tissue to be measured.

EMBODIMENT

Figure 6:
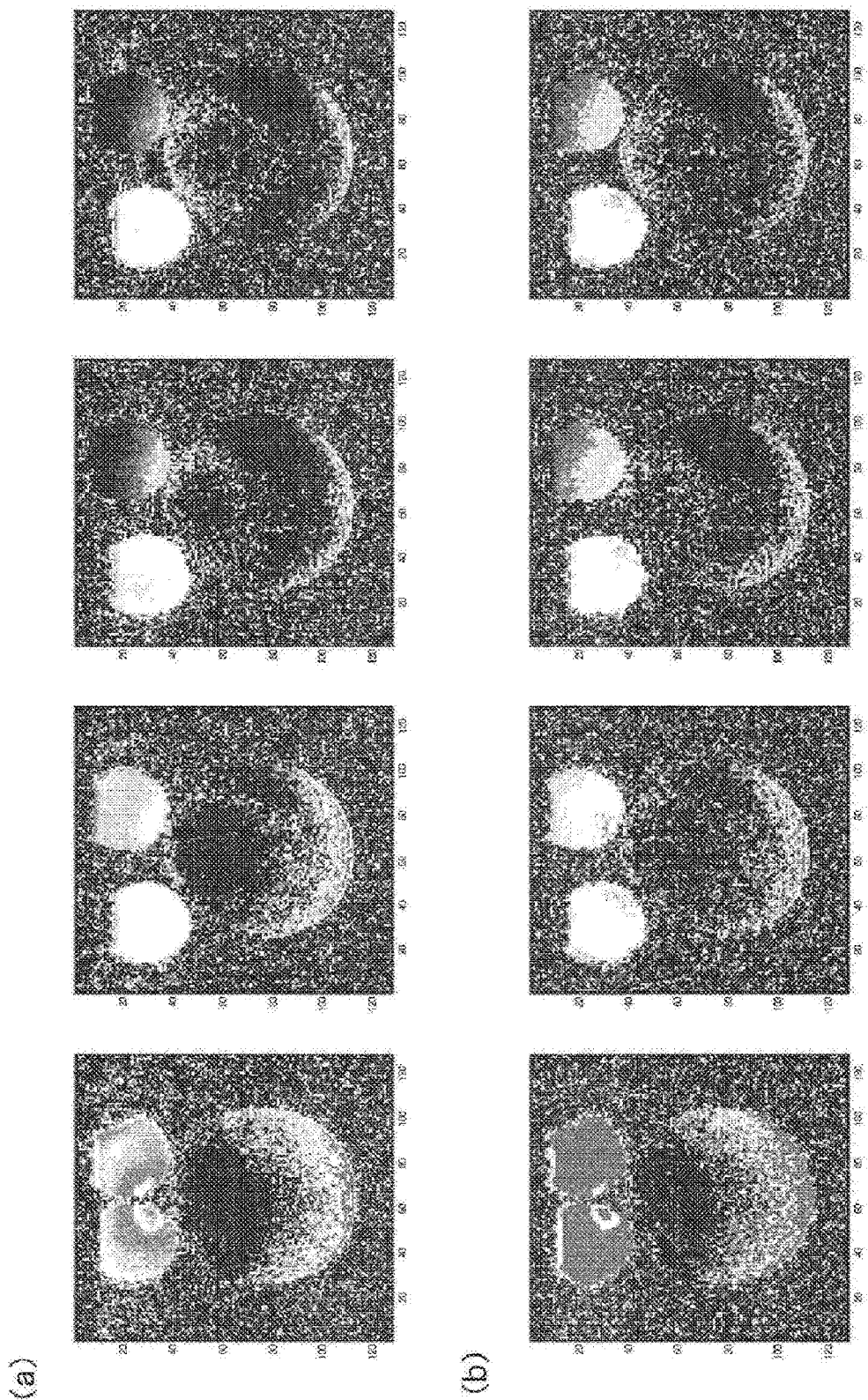
FIGS. 6 (a) and (b) are views illustrating the measurements performed according to an embodiment of the method for measuring the temperature distribution of the present invention, the former showing the temperature distribution images reflecting variation in temperature obtained from temperature measurement on the basis of the $CH_2$ group component signal by the method for measuring the temperature distribution of the present invention, and the latter showing the temperature distribution images reflecting variation in temperature obtained from temperature measurement on the basis of the $CH_3$ group component signal by the method for measuring the temperature distribution of the present invention.
Figure 7:
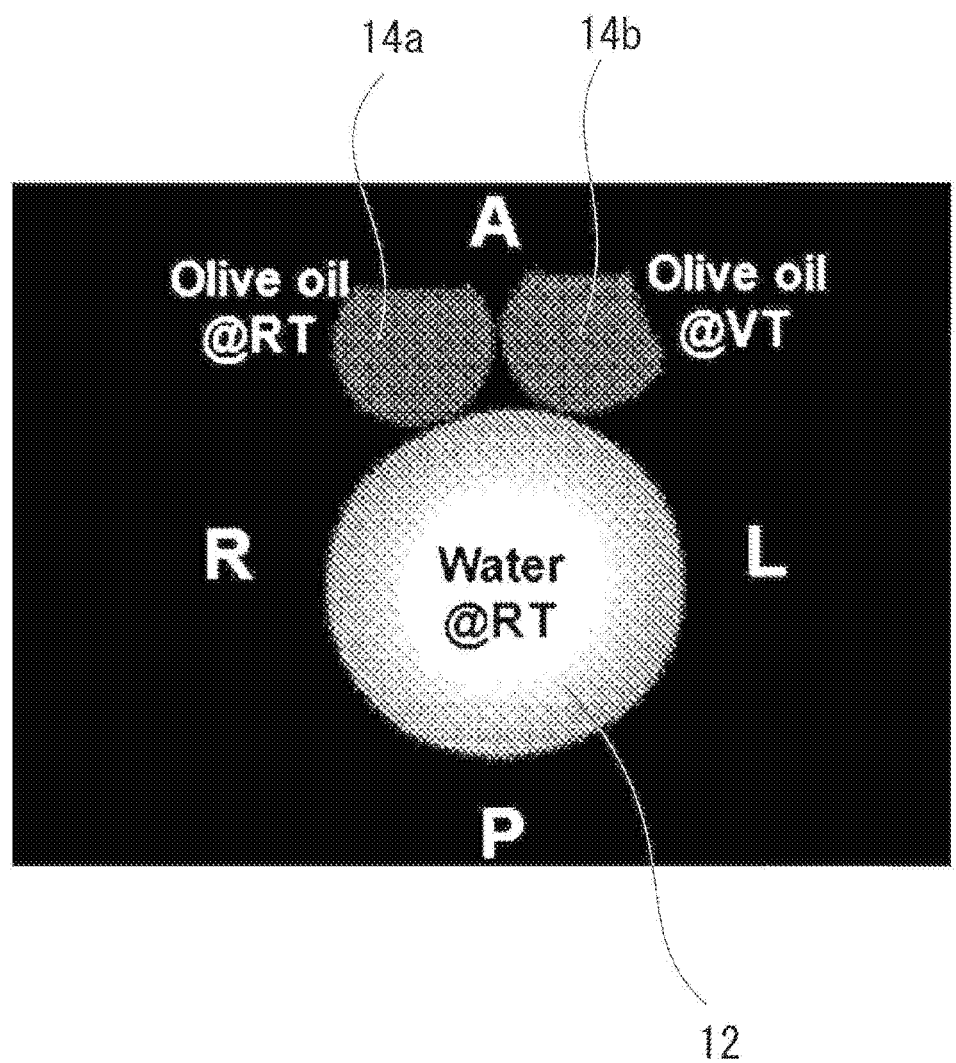
FIG. 7 is a view illustrating the structure of an object to be measured as shown in FIGS. 6 (a) and 6 (b).

FIG. 6 (a) shows the temperature distribution images reflecting variation in temperature measured on the basis of the $CH_2$ group component signal by the method for measuring the temperature distribution of the present invention, FIG. 6 (b) shows the temperature distribution images reflecting variation in temperature measured on the basis of the $CH_3$ group component signal by the method for measuring the temperature distribution of the present invention, and FIG. 7 illustrates the structure of the object to be measured as shown in FIGS. 6 (a) and 6 (b).

The object 10 to be measured in the embodiment is, as shown in FIG. 7, composed of a water part 12 and fat parts 14a, 14b. The water part 12 is a plastic case containing water and the fat parts 14a, 14b are plastic cases containing olive oil.

Here in initial condition, the water part 12 and the fat part 14a are at room temperature (@RT) and the temperature of the fat part 14b has been increased to 65° C. by microwave heating (@VT).

Then with the fat parts 14a, 14b being in contact with the water part 12, how the temperature changes was measured by the method for measuring the temperature distribution of the present invention.

As shown in FIGS. 6 (a) and 6 (b), variation in water temperature and variation in fat temperature may be measured accurately both when the temperature is measured on the basis of the longitudinal relaxation time of the $CH_2$ group component and when the temperature is measured on the basis of the longitudinal relaxation time of the $CH_3$ group component.

What is claimed is:

1. A method for measuring temperature distribution in tissue, comprising:
    dividing the tissue to be measured into measurement units of a given size;
    for each measurement unit,
        acquiring a water signal, which is dependent on water components of the tissue to be measured and a fat signal, which is dependent on fat components of the tissue to be measured using nuclear magnetic resonance spectroscopy and separating out the fat signal into various fatty acid components having a different hydrocarbon structure, so as to be used as various fatty acid signals; and
        measuring temperature of the high-water content tissue on the basis of a correlation between the water signal and water temperature, and measuring temperature of the fat tissue on the basis of a correlation between at least one of the various fatty acid signals and fat temperature.

2. The method for measuring the temperature distribution of claim 1,
    wherein, a weighted average of the water temperature and the fat temperature obtained for each measurement unit is calculated on the basis of the content of the water components and the content of the fat components in the tissue to be measured for each measurement unit, so as to be used as temperature of the tissue to be measured for each measurement unit.

3. The method for measuring the temperature distribution of claim 1, wherein, the temperature of the fat tissue is measured using a $CH_2$ group dependent signal or a $CH_3$ group dependent signal, among the various fatty acid signals.

4. The method for measuring the temperature distribution of claim 1,
wherein, a longitudinal relaxation time for each of the various fatty acid components is measured by any one of a multiple flip angle method, an inverse recovery method, and a saturation recovery method so as to be used as a correlation parameter between the various fatty acid signals and the fat temperatures.

5. The method for measuring the temperature distribution of claim 4,
wherein, the longitudinal relaxation time for each of the various fatty acid components and the water signal are measured simultaneously.

6. A method for imaging temperature distribution which creates temperature distribution images by converting the temperature highs and lows in the temperature distribution of the tissue to be measured, which is measured by the method for measuring the temperature distribution of claim 1, into signal intensity so as to be mapped.

* * * * *